United States Patent
Guggenmos et al.

(10) Patent No.: US 9,060,831 B2
(45) Date of Patent: Jun. 23, 2015

(54) DEVICE FOR PRODUCING A DENTAL WORKPIECE

(75) Inventors: Sebastian Guggenmos, Peissenberg (DE); Michael A. Kraemer, Landsberg am Lech (DE); Michael K. Schaaf, Herrsching (DE); Stefan Hoescheler, Munich (DE); Thomas Sprengart, Landsberg (DE); Martin Goetzinger, Eching am Ammersee (DE)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 512 days.

(21) Appl. No.: 12/524,786

(22) PCT Filed: Feb. 4, 2008

(86) PCT No.: PCT/US2008/052870
§ 371 (c)(1),
(2), (4) Date: Jul. 28, 2009

(87) PCT Pub. No.: WO2008/097874
PCT Pub. Date: Aug. 14, 2008

(65) Prior Publication Data
US 2010/0000677 A1   Jan. 7, 2010

(30) Foreign Application Priority Data

Feb. 6, 2007   (GB) .................................. 0702196.7

(51) Int. Cl.
*A41G 1/00* (2006.01)
*B29C 65/00* (2006.01)
(Continued)

(52) U.S. Cl.
CPC ....... *A61C 13/0022* (2013.01); *Y10T 156/1785* (2015.01); *Y10T 156/1798* (2015.01); *B29C 65/48* (2013.01); *B29C 65/7811* (2013.01); *B29C 65/7829* (2013.01); *B29C 65/7841* (2013.01)

(58) Field of Classification Search
CPC ............... A61C 13/00; A61C 13/0003; A61C 13/0004; A61C 13/0006; A61C 13/0027; A61C 13/08; A61C 13/083; A61C 9/0006; A61C 9/002; A61C 5/10; Y10S 269/909; Y10T 29/49567; B29C 65/48; B29C 65/4805; B29C 65/483; B29C 65/4835; B29C 65/485; B29C 65/78; B29C 65/7802; B29C 65/7805; B29C 65/7808; B29C 65/7811; B29C 65/782; B29C 65/7823; B29C 65/7829; B29C 65/7841
USPC ........... 156/60, 61, 89.11, 89.23, 94, 98, 153, 156/154, 196, 242, 245, 293, 294, 295, 156/303.1, 305, 349, 538, 573, 578; 433/25, 34, 36, 49, 53, 77, 141, 163, 433/167, 199.1, 201.1, 213, 215, 218, 223, 433/229; 264/16, 17, 19, 20; 425/2; 269/86, 269/257, 271, 279, 280, 282, 283, 287, 902, 269/909; 206/63.5, 363, 368, 369; 249/54; 451/364, 365
See application file for complete search history.

(56) References Cited

U.S. PATENT DOCUMENTS 549,274 A   11/1895   Melen
(Continued)

FOREIGN PATENT DOCUMENTS

CA   2280352   2/2000
(Continued)

OTHER PUBLICATIONS

Product Literature: 3M ESPE, "Lava®, Der Rohstoff für perfekte Vollkeramik", Scientific Affairs, Mar. 2001, pp. 6.
(Continued)

*Primary Examiner* — Philip Tucker
*Assistant Examiner* — Brian R Slawski

(57) ABSTRACT

The invention includes a support frame for producing a dental workpiece. The frame has a Z axis and comprising wall sections defining a hole that extends along the Z axis through the frame. At least one of the wall sections comprises an adhesive-directing surface extending along the Z axis in a non-parallel relationship. Such a configuration provides optimized methods for affixing a blank to the support frame and optimized properties of the blank after fixation to the support frame.

24 Claims, 7 Drawing Sheets

(51) Int. Cl.
*B32B 37/00* (2006.01)
*B32B 38/10* (2006.01)
*B29C 47/00* (2006.01)
*A61C 19/00* (2006.01)
*A61C 3/00* (2006.01)
*A61C 8/00* (2006.01)
*B23Q 3/00* (2006.01)
*A61C 13/00* (2006.01)
*B29C 65/48* (2006.01)
*B29C 65/78* (2006.01)

(56) References Cited

U.S. PATENT DOCUMENTS

| | | | |
|---|---|---|---|
| 1,796,470 | A | 3/1931 | Meyer |
| 1,899,718 | A | 2/1933 | Poston |
| 2,355,853 | A | 8/1944 | Foxon |
| 2,409,783 | A | 10/1946 | Moskey |
| 2,883,703 | A | 4/1959 | Raymond |
| 3,276,122 | A | 10/1966 | Slayton |
| 3,495,333 | A | 2/1970 | Kuhn |
| 3,664,785 | A | 5/1972 | Marshall |
| D278,744 | S | 5/1985 | Miener |
| 4,536,366 | A | 8/1985 | Inoue |
| 4,615,678 | A | 10/1986 | Moermann et al. |
| D297,762 | S | 9/1988 | Ito |
| 5,043,123 | A | 8/1991 | Gormanns |
| 5,135,393 | A | 8/1992 | Eidenbenz |
| 5,160,747 | A | 11/1992 | Kizaki |
| 5,259,744 | A | 11/1993 | Take |
| 5,306,673 | A | 4/1994 | Hermansson |
| 5,378,416 | A | 1/1995 | Kishi |
| 5,383,752 | A | 1/1995 | Rheinberger |
| 5,490,810 | A | 2/1996 | Hahn et al. |
| 5,551,856 | A | 9/1996 | Katagiri |
| 5,632,941 | A | 5/1997 | Mehrotra |
| 5,647,704 | A | 7/1997 | Turchan |
| 5,698,149 | A | 12/1997 | Hinzmann |
| 5,813,859 | A | 9/1998 | Hajjar et al. |
| 5,849,068 | A | 12/1998 | Hofmann |
| 6,074,584 | A | 6/2000 | Hinzpeter |
| 6,099,772 | A | 8/2000 | Hinzmann |
| 6,113,378 | A | 9/2000 | Tsuboi |
| 6,190,171 | B1 | 2/2001 | Hajjar et al. |
| 6,224,371 | B1 | 5/2001 | DeLuca |
| 6,454,568 | B1 | 9/2002 | Beuschel et al. |
| 6,641,340 | B1 | 11/2003 | Hajjar |
| 6,769,912 | B2 | 8/2004 | Beuschel |
| 6,905,293 | B1 | 6/2005 | Filser |
| 7,077,391 | B2 | 7/2006 | Filser et al. |
| D627,472 | S | 11/2010 | Wagner |
| D627,473 | S | 11/2010 | Wagner |
| D627,889 | S | 11/2010 | Wagner |
| 2002/0182566 | A1* | 12/2002 | Beuschel et al. ............... 433/163 |
| 2003/0031984 | A1* | 2/2003 | Rusin et al. .................... 433/215 |
| 2003/0132539 | A1* | 7/2003 | Althoff et al. ................... 264/16 |
| 2004/0072121 | A1* | 4/2004 | Filser et al. ..................... 433/25 |
| 2004/0168610 | A1 | 9/2004 | Conrad |
| 2010/0000677 | A1 | 1/2010 | Guggenmos |

FOREIGN PATENT DOCUMENTS

| | | |
|---|---|---|
| DE | 29815486 U1 | 2/2000 |
| DE | 4436231 | 1/2006 |
| EM | 1018766-1/3 | 11/2008 |
| EP | 0391446 | 10/1990 |
| EP | 0455854 | 11/1991 |
| EP | 0480238 | 4/1992 |
| EP | 0759728 | 11/1995 |
| EP | 0807422 | 11/1997 |
| EP | 0982009 | 3/2000 |
| JP | 10192305 | 7/1998 |
| JP | 2000-107202 | 4/2000 |
| WO | WO 95/30382 | 11/1995 |
| WO | WO 9530382 A1 * | 11/1995 ............... A61C 5/10 |
| WO | WO 01/97707 | 12/2001 |
| WO | WO 0245614 | 6/2002 |
| WO | WO 2007/141324 | 12/2007 |
| WO | WO 2008/000313 | 1/2008 |

OTHER PUBLICATIONS

Product Literature: 3M ESPE, "Lava™ CAD/CAM System für vollkeramische Restaurationen", May 2002, pp. 2.

Product Literature: 3M ESPE, No. 70200948852 / 01 (Apr. 2002), "Lava™ CAD/CAM System für vollkeramische Restaurationen", Apr. 2002, pp. 8.

Product Literature: 3M ESPE, Products 2003/2004, Catalog pp. 98-99.

Product Literature: ESPE Dental AG, "LAVA Prozesskette", (date unknown but believed to be earlier than the effective US filing date and any foreign priority date), pp. 1.

Product Literature: HintElis DentaCad Systeme, "Hint-Els® virus", Apr. 15, 2005, pp. 4.

Product Literature: HintEls DentaCAD Systems, "Trade Fair Offerings", Mar. 21, 2007, pp. 2.

Product Literature: IPS e.max, "all ceramic all you need", Mar. 2007, pp. 4.

Product Literature: KaVo Dental GmbH, "Reaching the peak of CAD/CAM performance", Mar. 21, 2007, pp. 4.

Product Literature: Kavo, "Kavo Everest® CAD/CAMSystem, Mit Materialviefalt an die Spitze.", (date unknown but believed to be earlier than the effective US filing date and any foreign priority date), pp. 12.

Product Literature: Kavo, No. 1003.8925 / 111/05, "Kavo Everest® Zirkonkeramik. Für exzellenten Zahnersatz", Apr. 15, 2005, pp. 10.

Product Literature: Schütz Dental GmbH, "Tizian™ CAD/CAM, Zirkon ohne Limit", Mandler Mar. 2007, pp. 3.

Product Literature: Schütz Dental GmbH, "Tizian™ Mill", Mandler Mar. 2007, pp. 5.

Product Literature: Sirona, Dispo—No. 04605, 201305C6026 WS 03078, "Mit inLab ist Erfolg immer ausbaufähig", Mar. 21, 2002, pp. 4.

Product Literature: Von Ekton, "CAD/CAM von etkon—Die Zahntechnik ist am Ziel.", Apr. 15, 2005, pp. 6.

Product Literature: Wieland Dental Division, No. 530075d.00.02.07, Das Zeno® Tec System, Feb. 2007, pp. 8.

Product Literature: Zirkon Zahn, "The Original", Mar. 2007, pp. 7.

Search Report for United Kingdom Application No. GB0702196, pp. 3.

Search Report for International Application No. PCT/US2008/052870, 3 pages.

User Newsletter: DeGuDent GmbH, "cercon smart ceramics", vol. 1, 2004, pp. 6.

Written Opinion of International Application No. PCT/US2008/052870, 5 pages.

* cited by examiner

DEVICE FOR PRODUCING A DENTAL WORKPIECE

CROSS REFERENCE TO RELATED APPLICATIONS

This application is a national stage filing under 35 U.S.C. 371 of PCT/US2008/052870, filed Feb. 4, 2008, which claims priority to German Application No. 0702196.7, filed Feb. 6, 2007, the disclosure of which is incorporated by reference in its entirety herein.

FIELD OF THE INVENTION

The present invention relates to a device for producing a dental workpiece from a blank, and in more particular to a device for producing a dental workpiece that is used to make a dental prosthesis like a crown or a bridge. Furthermore the invention is directed to a method of affixing a blank, from which the dental workpiece is obtained, to a support frame.

BACKGROUND OF THE INVENTION

In the field of dentistry, restoration of a patient's tooth or teeth that, for example, have been affected by caries generally includes the replacement of the natural tooth substance by an artificial substance. For larger restorations, pre-finished dental prostheses (such as inlays, crowns and bridges) are commonly used to replace at least a part of the tooth or teeth. The tooth to be repaired will be referred to only as a single tooth for simplicity, although it is possible that multiple teeth may be restored as part of the same procedure.

To restore a tooth, the dentist usually completely removes the decayed tooth material, and prepares the remainder of the tooth to receive a dental prosthesis. For example, if a crown will be used for the intended dental restoration, the tooth stump is commonly prepared so that it can be fitted with the crown using an adhesive.

The teeth of the patient are then usually replicated by taking an impression, and using the impression to make a plaster model. The model can be used to make, for example, a suitable dental prosthesis in a dental laboratory.

In recent years, dental prostheses have been produced using automated manufacturing processes such as milling or grinding. There are machines on the market for producing crowns and bridges and/or a precursor of it (herein generally referred to as dental workpiece) machined from a material blank by an automated process. For example, a system allowing computer controlled manufacturing of dental workpieces is available under the designation Lava™ CAD/CAD System, from 3M ESPE AG, Germany.

Typically the automated production of a dental prosthesis comprises the following steps.

First, a suitable system captures of the shape of the tooth or teeth of the patient. This can be done by scanning the plaster model of the patient's teeth, or alternatively by scanning the actual teeth in the patient's mouth. The scan data is normally used to create a virtual model of the prosthesis using software, for example computer-aided design (CAD) software. The software may provide data for computer-controlled manufacturing of a dental workpiece, for example the instruction data for controlling a milling or grinding machine.

In a second step, a milling or grinding machine machines the dental workpiece using the instruction data. The instruction data may be obtained from one of the steps mentioned above or otherwise, for example from a database comprising standard instructions for machining standard shapes. When machining the dental workpiece from the blank, the blank is normally affixed in a support frame and the support frame is held in position. This allows the dental workpiece to be positioned precisely during the machining operation. Usually the workpiece is connected to the remainder of the blank by webs to ensure that it is held in place during the machining operation. Typically the webs are rather small structures, so that the workpiece can be machined precisely without having the machine interfere with the webs. On the other hand, the webs are preferably big enough so that they can hold the workpiece securely in place during machining. When the workpiece has been fully machined, the webs are usually manually cut to separate the workpiece from the rest of the blank.

In a third step, the workpiece may be finally polished, or provided with a veneer, to form the finished prosthesis.

A prosthesis made based on a computer-controlled machined workpiece is generally very precise and can usually be applied to the prepared tooth or teeth by the dentist without extensive adaptation. The prosthesis usually consists of a very durable and biocompatible material, and it is affixed to the prepared tooth using an adhesive.

DE 298 15 486 U1 discloses a device for producing a dental workpiece having a blank and a support body. The blank is accommodated within a recess of the support body. The support is designed so that the blank does not extend beyond the support body in any direction.

In US 2003/0132539 a device for automated production of dental workpieces is disclosed. A blank is inserted into a support. The blank is linked with only opposite inner walls of a recess provided within the support. A gap is left between the blank and the other walls. The design is supposed to avoid tensions and micro-cracks within the blank material.

SUMMARY OF THE INVENTION

In a first aspect of the invention a support frame for producing a dental workpiece is provided. The support frame has a Z axis and comprises wall sections defining a hole that extends along the Z axis through the frame. At least one of the wall sections comprises an adhesive-directing surface extending along the Z axis in a non-parallel relationship and preferably thereby diverging by at least 2 mm from the Z axis. Preferably the through-hole extends between a top and a bottom of the support frame.

Another embodiment of the invention may include an adhesive-directing surface that diverges from the Z axis by a dimension of between 1 and 10 mm, more preferably by a dimension of between 2 and 5 mm and preferably by 3 mm.

The adhesive-directing surface is preferably non-parallel to the Z axis and has a tangent that is angled relative to the Z axis by at least 5 degrees. This means the adhesive-directing surface may be curved or beveled but preferably has a tangent on the surface that is angled relative to the Z axis.

An embodiment of the invention may include an adhesive-directing surface that is non-parallel to the Z axis and has a tangent that is angled relative to the Z axis by between 5 and 90 degrees, more preferably by between 5 and 30 degrees and preferably by 10 degrees.

The at least one wall section defining the through hole may also form a fixation wall for affixing a blank within the through-hole. Preferably the fixation wall further comprises a bonding zone adjacent the adhesive-directing surface. Further, the support frame may comprise the blank, wherein the blank is affixed at the fixation wall by adhesive bond with at least the bonding zone. The dental workpiece may be obtained from the blank, for example by milling.

In a preferred embodiment of the invention, the adhesive-directing surface provides at least a part of the through-hole that narrows from an exterior towards an interior of the through hole, and preferably thereby provides for formation of a constriction within the through-hole.

In another preferred embodiment the adhesive-directing surface due to its shape, is adapted to direct a flowable adhesive received on the adhesive-directing surface toward the bonding zone and thereby toward the blank.

The adhesive-directing surface may be oriented substantially vertically in case the support frame is placed with its bottom on a horizontal surface, so that the Z axis of the support frame is vertical relative to the surface. Furthermore, the adhesive-directing surface may be shaped so that it allows an adhesive to be dispensed onto it easily, but once the adhesive is received on the surface it flows downward (toward the bottom of the support frame) and meets the blank to bond the blank to the fixation wall at at least the bonding zone. Dispensing adhesive onto the adhesive-directing surface may, for example, be done with the aid of an adhesive dispensing device from above the support frame. Such a dispensing device may, for example, have a dispensing needle which typically has an outlet of 1 to 1.5 mm. The dispensing needle is preferably aligned vertically, and with the adhesive-directing surface diverging from the Z axis, for example by at least 2 mm, a needle of such dimension can be used conveniently in cooperation with an adhesive-directing surface as described herein.

In a preferred embodiment, the shape of the adhesive-directing surface is at least partially convex, whereas in another embodiment the shape of the adhesive-directing surface may comprise a beveled portion. Convex (for example curved) and beveled structures may also be combined to form a shape that is adapted to direct a flowable adhesive received on the adhesive-directing surface toward the bonding zone and thereby toward the blank.

The fixation wall may comprise an optional flow advancing area which is adapted for facilitating adhesive flow, and an optional flow retarding area adapted for hindering adhesive flow. The advancing area may comprise grooves oriented substantially in the direction of the expected flow of the adhesive, and the retarding area may comprise grooves that are oriented generally transverse to the adhesive flow. The retarding area may also or instead comprise a roughened surface so as to hinder the adhesive flow. The fixation wall may also be modified to reduce or increase its wettability, and therefore to facilitate or hinder the flow of the adhesive. Such a surface modification may be done, for example by plasma treatment of the fixation wall or sections of it. Preferably at least a part of the flow advancing area is arranged on the adhesive-directing surface, and at least a part of the flow retarding area is arranged on the bonding zone, so that the adhesive flows over the adhesive-directing surface and stops in the bonding zone.

In another embodiment the through-hole may comprise an adhesive barrier to hinder or prevent adhesive that flows between the fixation wall and the workpiece from flowing to or toward an undesirable location, for example past the adhesive barrier. Preferably this adhesive barrier is a structure which is arranged on the fixation wall, for example on the bonding zone or on the adhesive-directing surface. The adhesive barrier may also be part of the fixation wall. In particular the adhesive barrier may be arranged on the fixation wall along at least a part of the length of the through-hole. In other words, the adhesive barrier may be arranged transverse to the expected flow direction of the adhesive. The adhesive barrier may be an edge or bulge, for example.

A further embodiment provides a support frame that has two opposed fixation walls for affixation to two surfaces of the blank, for example for affixation to two opposed surfaces of the blank. Each of the fixation walls may comprise an adhesive-directing surface and, adjacent, a bonding zone. The blank is preferably affixed with at least one fixation wall by an adhesive. Alternatively the blank is affixed at both of the opposing fixation walls by an adhesive. In particular the blank is preferably affixed at the bonding zones of the opposing fixation walls by an adhesive.

The adhesive preferably affixes the blank along a line, preferably by a strand of adhesive along a line that extends substantially over the length of the blank. However the blank may also be affixed by one or more adhesive points along at least a part of the length of the blank. Strands and points of adhesive may be combined to affix the blank to the support frame. Preferably, if no adhesive is present, there is clearance between the blank and the through-hole of the support frame. It is furthermore preferred that the fixation of the blank is caused substantially by the adhesive bond and more preferably is caused only by the adhesive bond. The blank thus preferably is tightly affixed to the support frame so it cannot move relative to the frame. Optionally, the adhesive is elastic so that it may act as a shock absorbent for the dental workpiece in case it is transported, for example when it is sent from the dental laboratory to the dentist. In that case the machine may provide an additional fixation of the blank or workpiece during machining, for example the blank and/or workpiece may be additionally held or clamped during machining so that the blank does not move.

In one embodiment the through-hole in a plane perpendicular to the Z axis has a cross-section of a generally rectangular shape. The through-hole may instead be generally circular, or of any other suitable shape. In case of a hole having only one continuous wall, for example a hole with a circular or elliptical cross-section, the "wall sections" defining the through-hole may correspond to virtual segments of the continuous wall, such as quarter sections of the continuous wall.

In a further embodiment a projection of the blank in a direction of the Z axis onto a plane perpendicular to the Z axis is generally rectangular. This includes, for example, a profile with a cross-section of a certain shape extending over a certain length, for example a cylinder or a cuboid. Other cross-sections may include a trapezoid, a hexagon or any other regular or irregular polygon.

The projection of the blank has a width and a length. The width and length correspond to actual dimensions of the blank that are further referred to as the width and the length of the blank respectively. Preferably one of the width and the length is smaller than the narrowest width of the through hole which corresponds to the space between the fixation walls. The narrowest width of the through hole may in more particular correspond to the space between the bonding zones of the fixation walls. Preferably the width of the blank is smaller by between 0.5 to 1.5 mm than the space between the bonding zones. It is further preferred that the length of the blank is smaller than the corresponding length of the through hole. Preferably the length of the blank is smaller by between 2 to 10 mm. In other words, there may be clearance between the blank and the support frame when the blank is accommodated in the through-hole of the support frame and when no adhesive is present. Such clearance may be 0.5 to 1.5 mm in a dimension along the width of the blank, and between 2 to 10 mm in a dimension along the length of the blank. The clearance may be a total clearance composed of partial clearances on opposite sides of the blank.

The support frame may comprise at least one spacer within the through-hole for positioning the blank within the through-hole. The spacer preferably spaces the blank away from a wall section defining the through-hole. More preferably the support frame comprises more than one, preferably 2 or 4 spacers, which centers the blank within at least the length and preferably also within the width of the through-hole. These spacers may be removed prior to machining the blank, or they may remain in place. The blank may, however, also be positioned without spacers within the through-hole. In this case the machine may recognize the relative position of the blank within the support frame which, for example, can be used as offset dimensions for positioning the milling or grinding tool when the dental workpiece is manufactured.

The blank is preferably made of a pre-sintered ceramic material, like zirconium oxide. The blank may further be a composite material, which is basically a composition of methacrylate and a filler (for example silica, alumina, circonia).

The adhesive may be one of a chemically curing and thermosetting adhesive. Preferably the adhesive is an epoxy-based adhesive, for example the adhesive available under the designation DELO-DUOPOX® 03 RAPID, from the DELO company, Germany. It is also possible to use hot-melt adhesives.

In a preferred embodiment, the support frame is adapted to be automatically handled in a machine for processing blanks prior to, during, and after milling. This means the support frame may have dimensionally stable guiding surfaces that can, for example, be grasped, clamped, moved or positioned by a machine. One example of a suitable machine is the LAVA™ Form, which is a component of the system sold by 3M ESPE Dental under the designation LAVA™. In a preferred embodiment the support frame comprises at least one feature allowing automatic detection of the orientation of the support frame, for example a chamfer at an edge of the frame, such that any frame that is not positioned correctly is rejected, or is automatically repositioned correctly. Furthermore, the support frame may comprise ridges arranged at outer surfaces, for example outer side walls, of the support frame that may be clamped to fix the support frame or used to guide the support frame in the machine. The support frame is further preferably dimensioned so that the blank does not extend beyond the support frame in any direction. In particular the blank preferably does not extend beyond the top and the bottom of the support frame. Alternatively the blank is dimensioned so that its height corresponds to the height of the frame. The height in this regards is the dimension between the top and the bottom of the frame. As an advantage this alternative embodiment preferably allows the blank to be positioned in the support frame without positioning it differently than the frame in the Z axis. For example, the support frame with the blank may just be placed on a plane surface together to position both parts in the Z axis correctly relative to each other.

In another embodiment the support frame comprises a machine readable code. This may be, for example, an optically scannable pattern, like a barcode. The code may be stored in a transponder associated with the frame and/or blank, which is adapted to communicate with an electronic reader of the machine. The code may be used to load a dataset from a database which, for example, may comprise instructions for the machine to produce the workpiece. Further the code may be used to obtain logistics data from a database like, for example, the address of the dentist to whom the finished dental prosthesis may be sent. The code may also comprise data about the position of the blank relative to the frame, for example an offset that can be used to calculate the position of the blank relative to the position of the frame.

The support frame may have visible indicia. The support frame may be marked, for example, with letters or a symbol that can be recognized by an operator or an optical recognition device. Such indicia may be arranged at an outer surface of the support frame and may be colored and/or embossed or recessed.

In a preferred embodiment the support frame is molded. Preferably the support frame is made of polystyrene (PS), however it may also be made of polycarbonate (PC), acrylonitrile-butadiene-styrene (ABS), polybutadiene terephthalate (PBT), polymethyl methacrylate (PMMA), polyoxymethylene (POM) or any other suitable polymer. The polymer may be fiber-reinforced. It may, however, also be provided that the support frame is made of other materials, like a thermosetting material or metal, for example.

In a further aspect the invention is directed to a method of affixing a blank within a support frame, comprising the steps of
(i) positioning a blank within a through-hole of a support frame;
(ii) dispensing adhesive on an adhesive-directing surface of the support frame and preferably keeping the blank free of adhesive; and
(iii) causing the adhesive to flow toward the blank and contact the blank.

The adhesive is preferably dispensed by a dispensing device having a dispensing needle which is movable relative to the support frame. Preferably the adhesive is dispensed on the adhesive-directing surface near the top of the support frame by continuously dispensing adhesive while moving the needle continuously along the adhesive-directing surface. Thus a line of adhesive is deposited on the adhesive-directing surface, and from there is able to move toward the blank. Alternatively the adhesive may be deposited on the adhesive-directing surface as individual drops. The deposited adhesive preferably flows towards the blank because of its own mass and flow characteristics. In other words, the adhesive may be dispensed on a deposition area from which it flows down the adhesive-directing surface to the bonding zone where it meets the blank. In this regard the deposition area is a part of the adhesive-directing surface. The deposition area is preferably the upper 20% to 30% of the adhesive-directing surface, meaning the part of the surface that is arranged adjacent the top of the support frame. Preferably the amount of the adhesive deposited on the adhesive-directing surface is determined based on how much of that adhesive flows across the adhesive-directing surface until it meets the blank. If the blank is spaced away from the bonding zone of a fixation wall, the amount of adhesive may be determined so that it bridges the clearance between the blank and the bonding zone when the adhesive reaches the clearance. Preferably, the clearance is smaller than 0.5 mm and the viscosity of the adhesive is at least 14,000-18,000 mPa s.

An adhesive may instead be provided on the adhesive-directing surface as a generally non-flowable deposit, for example a hot-melt. In this case energy may be applied, for example by the application of heat, ultrasound, vibration, radio frequency energy or UV light, to initiate flow of the adhesive. Providing a generally non-flowable deposit on the adhesive-directing surface may also include that the adhesive is placed on the adhesive-directing surface when it is flowable and solidifies generally in place, after which energy may be applied and the flow initiated. Such a support frame already prepared with a generally non-flowable deposit of adhesive may be pre-manufactured and subsequently combined with the blank. For example, the prepared support frame may be placed around a blank and the adhesive may be made to flow, for example by heating the adhesive or the whole support frame and blank in an oven, so that the adhesive flows down to the blank, and then cools or otherwise solidifies. This could, for example, permit a manufacturer to obtain a frame from one supplier and a blank from another supplier, and then to combine them.

A corresponding method of affixing a blank at a fixation wall within a support frame, preferably comprises the steps of:
(i) placing adhesive on the adhesive-directing surface of the support frame as a generally non-flowable deposit;
(ii) positioning a blank within a through-hole of a support frame; and
(iii) causing the adhesive to flow towards the blank and contact the blank.

In another aspect of the invention a magazine is provided, the magazine comprising multiple support frames, including at least one support frame according to the invention. Preferably the magazine comprises a member to engage with a chamfered corner or other feature of the support frame. This feature facilitates detection of the orientation of the support frame so as to permit only one correct orientation of the frame within the magazine. However, in case the support frame is designed to be used in two or more designated orientations, the magazine may be adapted to permit these designated orientations of the support frame within the magazine. Further the magazine may comprise an orientation feature allowing automatic detection of the orientation of the magazine by a machine for producing a dental workpiece, for example by a milling machine. The machine may recognize the orientation of the magazine and only permit correctly oriented magazines, and therefore correctly oriented support frames, to pass into the machine. This ensures that the workpiece is machined from the blank from the correct perspective.

Still another aspect of the invention is directed to a machine for producing a dental workpiece comprising the magazine of the invention. The milling machine preferably is adapted to recognize the orientation of the magazine by sensing the orientation feature. Preferably the machine for producing a dental workpiece is a milling machine.

Further, the invention is directed to a kit comprising a device for producing a dental workpiece and a milling tool. Preferably such a kit comprises at least one milling tool and more preferably a set of milling tools.

As a preferred advantage the support frame of the invention minimizes contamination of the blank surface with adhesive. This is advantageous because it is generally desired to keep the adhesive away from the machine tools used to mill the dental workpiece. For example, the cutting characteristics of milling or grinding tools, if used for machining of the dental workpiece, would probably be adversely affected by contact with an adhesive. Because the adhesive is dispensed on a deposition area which is preferably located a distance from the blank itself, contamination of the blank with the adhesive is minimized, and therefore tool performance may be improved by use of the invention.

Another preferred advantage is that the configuration of the adhesive-directing surface(s) allows easy dispensation of the adhesive. The deposition area may be arranged so as to allow dispensation of the adhesive with a straight vertical needle, in contrast to the prior art, which is a desirable configuration for a dispensing system with regard to precision and reliability of dispensation.

As a further preferred advantage the adhesive can be easily dispensed onto the support frame when it is placed with the major plane of the frame positioned generally horizontally. This allows the support frame to be placed on a generally horizontal surface with the blank being loosely arranged within the through-hole. As a result, Z-axis positioning of the blank relative to the frame may not be necessary.

DETAILED DESCRIPTION OF THE INVENTION

Figure 1:
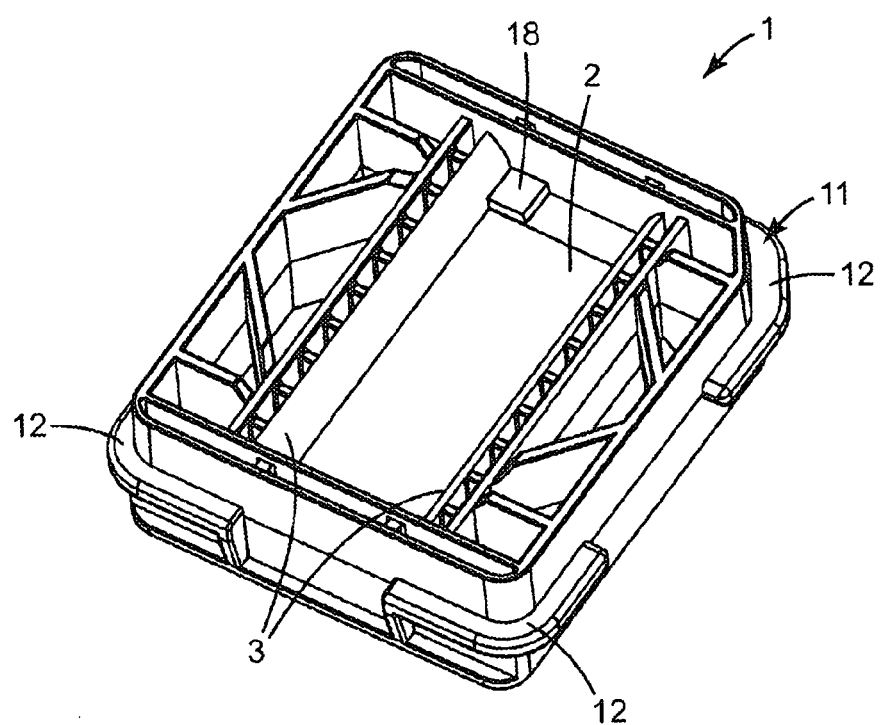
FIG. 1 shows a perspective view of a support frame according to the invention.

FIG. 1 shows a support frame 1 defining a through-hole 2. The support frame 1 comprises fixation walls 3 which are of a generally convex, in particular circular shape. A spacer 18 is arranged within the through-hole, which may be used to position the blank in the through-hole. Further spacers may be arranged in the other corners of the through-hole or at any of the wall sections defining the through-hole. The support frame 1 comprises a chamfer 11 at a corner of the frame which may be used, for example to detect orientation of the support frame in a machine for automatic handling. Further, the support frame comprises ridges 12 for guiding and/or clamping the support frame in the machine. The support frame is preferably formed by walls of a similar thickness which is especially advantageous for molding the support frame of plastic. In the example shown this is achieved by using webs to make up larger portions of the support frame instead of making those portions solid. The webs are further also designed to make the support frame relatively stiff, for example to avoid bending or twisting when exposed to applied forces. Generally all walls including the webs are arranged so that the support frame can be molded by a relatively simple mold, meaning that the support frame is designed generally without undercuts that would prevent a mold component from being removed.

Figure 2:
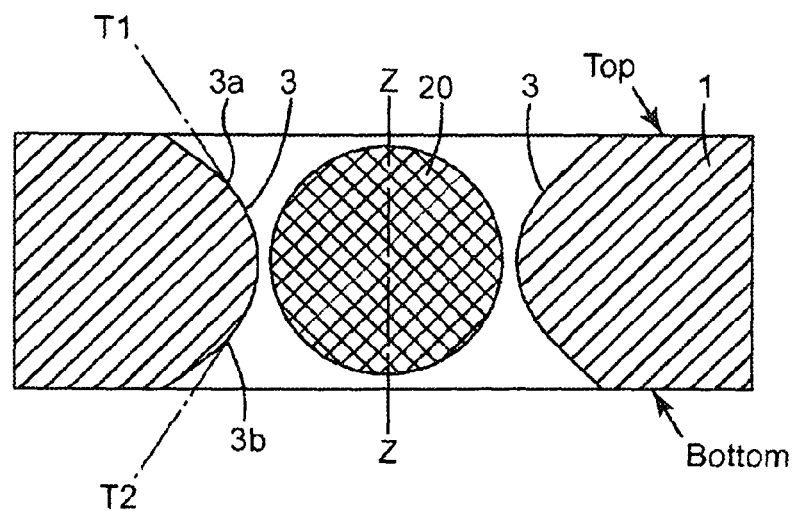
FIG. 2 shows a perspective view of a support frame according to the invention, with a blank accommodated in the through-hole.

FIG. 2 shows a cross-section of a support frame 1 with a blank 20 accommodated in the through-hole which extends along a Z axis. The fixation walls have adhesive-directing surfaces 3a, 3b and a bonding zone between (not specifically identified in the figure). The beginning and the end of the bonding zone and the adhesive-directing surface may be structurally continuous, segments along a continuous surface or segments on discrete surfaces. The adhesive-directing surfaces continue along the Z axis in a non-parallel relationship and thereby diverge from the Z axis. In this case the adhesive-directing surfaces have a generally convex cross-sectional shape, in particular an arc of a circle. It can also be seen that tangents T1 and T2 on the adhesive-directing surface are angled relative the Z axis.

Figures 3A, 3B:
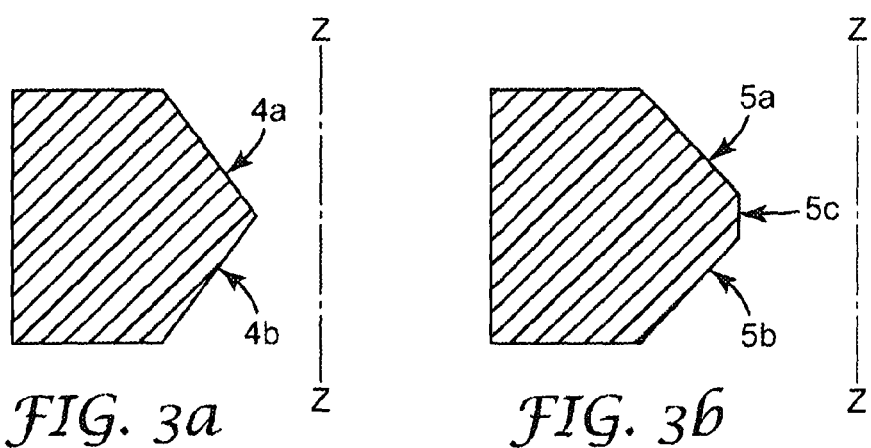
FIGS. 3a, 3b shows cross-sectional views of alternative shapes of the fixation wall of the support frame according to the invention.

FIG. 3a and FIG. 3b show alternative cross-sectional embodiments of the fixation wall with adhesive-directing surfaces and a bonding zone. In FIG. 3a the adhesive-directing surfaces 4a, 4b are beveled portions which merge to form a substantially sharp edge around which the bonding zone may be established (not specifically identified in the figure). This may be advantageous relative to a convex shape of the adhesive-directing surface because the slope of each of the beveled portions is generally constant so that an adhesive flowing down the adhesive-directing surface might flow at a relatively uniform rate. In FIG. 3b the adhesive-directing surfaces 5a, 5b are also beveled portions but they merge with a third portion 5c that is generally aligned parallel to the Z axis and includes at least a part of the bonding zone. Portion 5c may be advantageous relative to the embodiment of FIG. 3a to hinder adhesive dispensed onto the fixation wall from flowing through a certain clearance that might exist between the bonding zone and the blank. This may be achieved because the portion 5c may better conform to the shape of the blank than the sharp edge of FIG. 3a so that the adhesive has to overcome a longer distance within the bottleneck.

Figure 4:
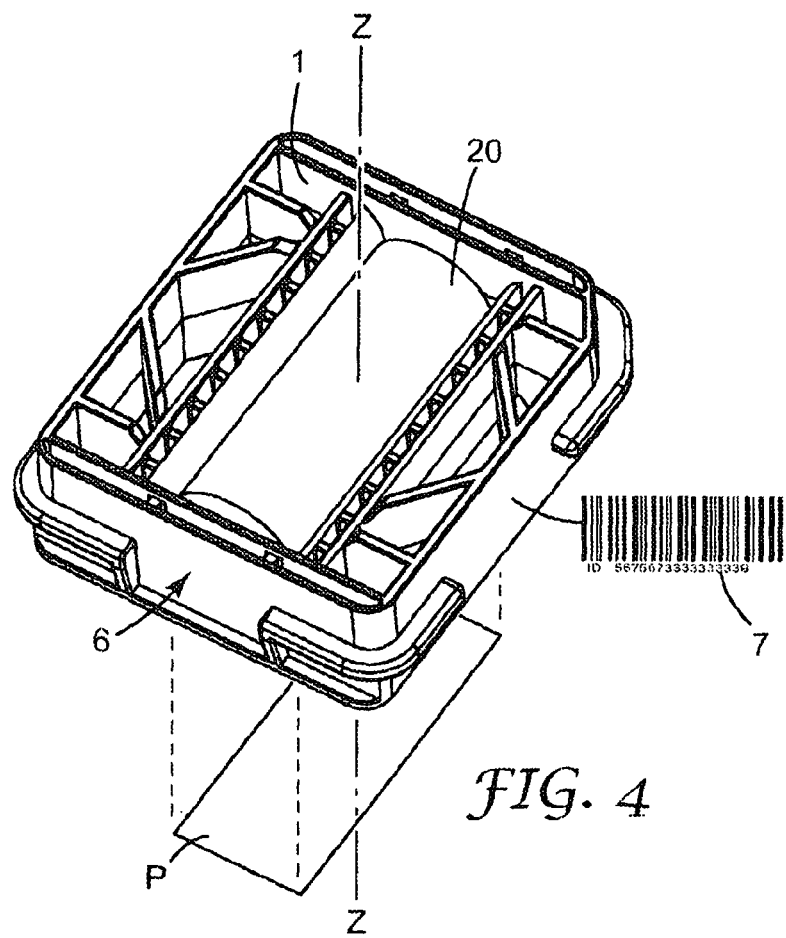
FIG. 4 shows a perspective view of a support frame according to the invention, with a blank accommodated in the through-hole.

FIG. 4 shows a support frame with a blank retained in the through-hole. The blank of this example is generally cylindrical. Blanks having other shapes may be used, for example blanks having a rectangular, hexagonal or other suitable shapes. As indicated, a projection "P" of the blank in a direction of the Z axis onto a plane perpendicular to the Z axis is generally rectangular. The support frame may comprise a machine readable code 7 or indicia 6 (not shown) or both. The machine readable code 7 may be used for identification of the material type of the blank. Further it may be used to identify a finished dental workpiece so that it, for example, can be assigned to the proper patient. The indicia may help a user to visibly identify the general type of material or the general type of the workpiece, for example to distinguish between a relatively large workpiece for a (multiple-tooth) dental bridge and a smaller workpiece for a (single-tooth) dental crown.

Figure 5:
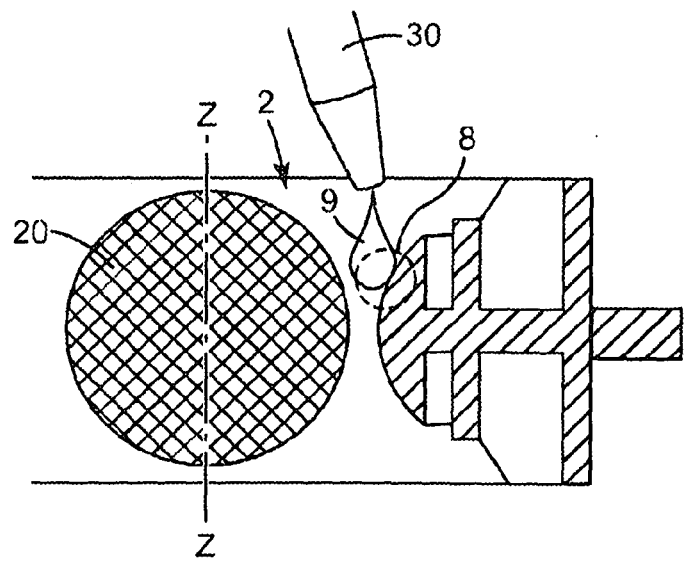
FIG. 5 shows a perspective cross-sectional view of a support frame according to the invention, with a blank and a dispensing needle dispensing adhesive on the adhesive-directing surface.

FIG. 5 shows a section of a support frame with a blank 20 as a cross-sectional view which also shows an embodiment in which the blank does not extend beyond the support frame in any direction. Therefore the support frame provides certain protection of the blank when it is handled, for example during shipping or in a machine. Further this configuration allows, for example, stacking of multiple support frames while preventing contact between the blanks of adjacent pieces. Further, FIG. 5 shows an adhesive 9 that is dispensed on a deposition area 8 by a dispensing needle 30. As can be seen the design of the adhesive-directing surface allows dispensation of the adhesive 9 with a conventional dispensing needle 30 because the deposition area 8 is generally accessible through the through-hole 2 from the top of the support frame. It can also be seen that the adhesive-directing surface diverges from the Z axis sufficiently to permit the dispensing needle to access the deposition area. The extent to which the adhesive-directing surface diverges from the Z axis may, however, be greater or lesser than shown.

Figure 5A:
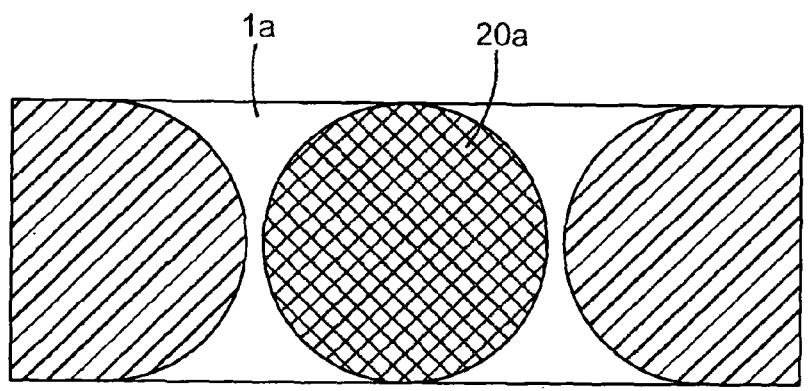
FIG. 5a shows a schematic cross-sectional view of a support frame and a blank according to an alternative embodiment of the invention.

FIG. 5a shows an embodiment of a support frame 1a and a blank 20a having substantially the same height. This may be of advantage because the blank may be positioned in the support frame without positioning it differently than the frame in the Z axis.

Figure 6A:
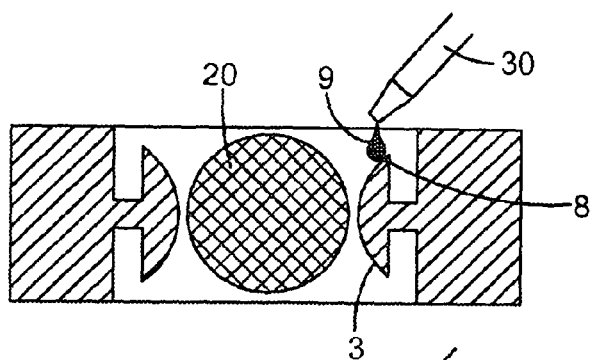
FIGS. 6a-6e show a schematic description of the method of fixing a blank in the support frame according to the invention.
Figure 6B:
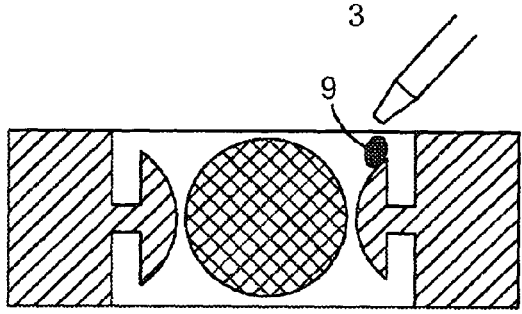
Figure 6C:
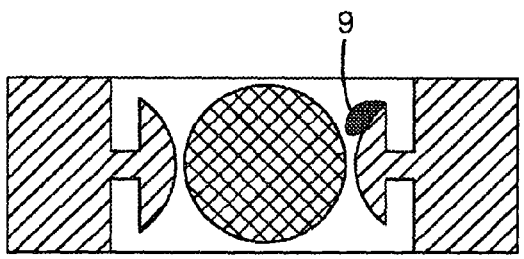
Figure 6D:
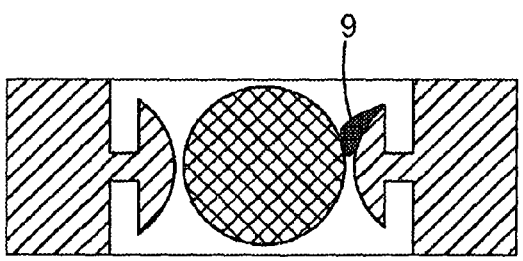
Figure 6E:
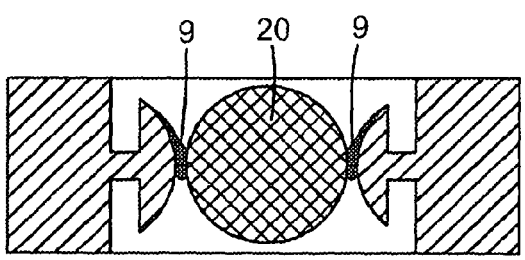

FIGS. 6a to 6e illustrate the method of affixing the blank 20 with an adhesive 9. In FIG. 6a an amount of adhesive is dispensed on the deposition area 8 of an adhesive-directing surface 3. The blank at least at this stage may be held by a device which is not shown for better clarity. The adhesive is dispensed as a droplet or a plurality of droplets. However, alternatively the adhesive may also be dispensed as a strand along at least a part of the length of the adhesive-directing surface. FIG. 6b shows the situation shortly after the dispensation of the adhesive has been finished. The liquid adhesive 9 has separated from the dispensing needle. In FIG. 6c the adhesive 9 has started to flow down the adhesive-directing surface and in FIG. 6d the adhesive has met the blank. The amount of adhesive as well as the flow characteristics of the adhesive are preferably determined so that the adhesive stops flowing when it has reached the bottleneck between the blank and the fixation wall. This is shown in FIG. 6e. In particular the adhesive in FIG. 6e has flown into the clearance between the blank and a bonding zone and stopped flowing in the bonding zone. In this way a good bond between the fixation wall and the blank is achieved as soon as the adhesive has hardened. FIG. 6e also illustrates a situation in which the blank 20 has been affixed to the fixation walls 3 on two opposite sides, for example by repeating the steps shown in FIGS. 6a-6d on the opposite side of the workpiece.

Figure 7:
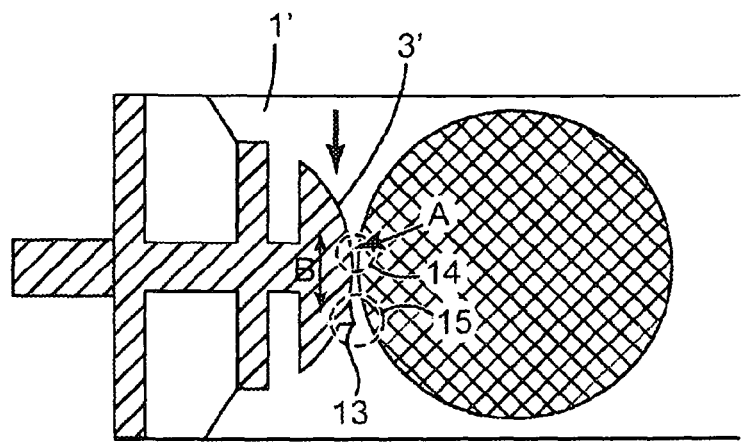
FIG. 7 shows a perspective cross-sectional view of a support frame according to the invention, with an adhesive barrier.

FIG. 7 shows the support frame 1' having a fixation wall 3' comprising an adhesive barrier 13. The adhesive barrier 13 forms a second bottleneck 15 between the blank and the fixation wall, thus additionally hindering adhesive if it passes the first bottleneck 14. Preferably the first bottleneck 14 is formed at a distance between the fixation wall or bonding zone and the blank of between 0.25 and 0.75 mm, and second bottleneck 15 is formed at a distance between the adhesive barrier 13 and the blank preferably of between 0.1 and 0.5 mm. The adhesive barrier 13 is preferably arranged below the bonding zone at a distance of between 1 and 3 mm.

Figure 8:
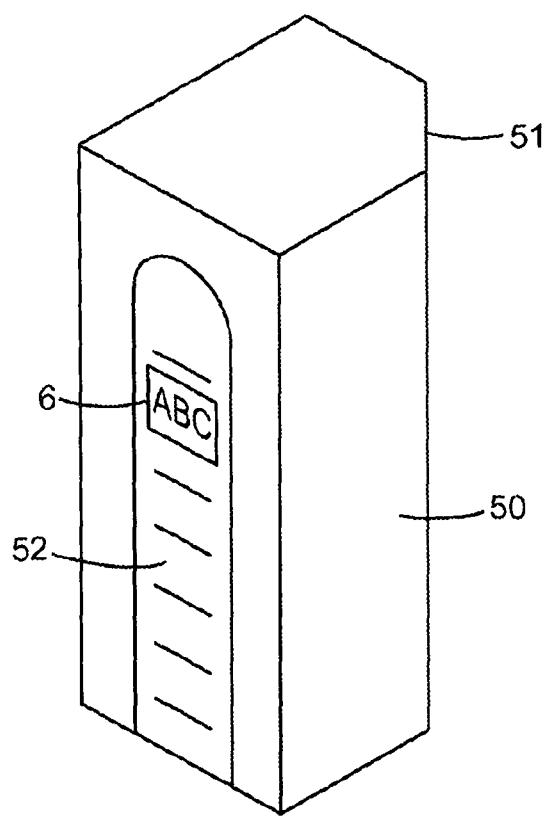
FIG. 8 shows a schematic perspective view of a magazine according to an embodiment of the invention.

FIG. 8 shows a magazine 50 for receiving the support frames according to the invention. A flattened edge 51 of the magazine allows the support frames to be inserted only in the correct orientation. A recess 52 in the magazine enables a user to observe the indicia 6 when the support frames are stacked in the magazine. An operator of a machine in which such magazine is used can thereby identify support frames containing, for example, different types of blanks or dental workpieces.

Figure 9:
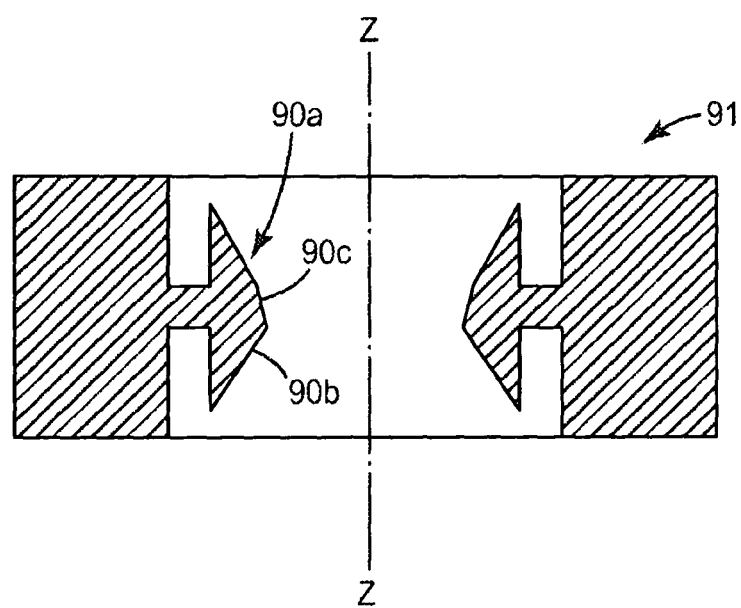
FIG. 9 shows a cross-sectional view of a support frame having an alternatively shaped fixation wall according to an embodiment of the invention.

FIG. 9 shows an alternative embodiment of a support frame 91 which has a fixation wall with adhesive-directing surfaces and a bonding zone. The embodiment shown is similar to the embodiment shown in FIG. 3b, with the adhesive-directing surfaces 90a and 90c being beveled portions merging with a third portion 90c. In contrast to FIG. 3b the portion 90c of embodiment of FIG. 9 is inclined with respect to the Z axis. However, the portion 90c also includes at least a part of the bonding zone. The angles of the portions 90a, 90b, and 90c relative to the Z axis may be 20° to 40°, and are preferably 30° for the portions 90a and 90b, and may be 2° to 22°, and is preferably 12° for the portion 90c. The portion 90c may help to hinder adhesive dispensed onto the fixation wall from flowing through a certain clearance that might exist between the bonding zone and the blank (not shown). In a preferred embodiment the transition between the portions 90b and 90c forms the narrowest portion between the opposing fixation walls. Preferably this narrowest portion is positioned about 2.5 mm offset from the center line of the support frame 91 with regard to its height. In more particular when the support frame is used with a blank (not shown) the narrowest portion is positioned about 2.5 mm offset from the center line of the blank with regard to its height. It has been found that the angle of the portion 90c relative to the Z-axis and the selected offset position of the narrowest portion may help to position the adhesive at about the center line of the blank with respect to its height. A fixation of the blank at the center line may be advantageous in case the blank is machined from opposite sides (from the bottom and the top in the figure), for example.

The present invention has been described with reference to several embodiments, but the invention shall not be limited by those examples, but only by the following claims and the equivalents thereof.

The invention claimed is:

1. A device, comprising:
    a support frame for producing a dental workpiece, the frame having a Z axis and comprising wall sections defining a through hole that extends along the Z axis through the frame, wherein at least one of the wall sections comprises an adhesive-directing surface having a generally convex cross-sectional shape, wherein the support frame has a T-shaped cross section supporting the convex surface near an adhesive deposition area;
    at least one spacer on the wall sections, wherein the spacer does not extend across the entire through hole in any direction; and
    a blank, wherein at least one of the wall sections forms a fixation wall for affixing the blank within the hole and positioned by the spacer, and wherein, when no adhesive is present, the blank can be accommodated in the hole in such a way that there is clearance between the blank and the fixation wall, wherein the width of the blank is smaller than the narrowest width of the through hole,
    wherein the blank has no direct contact with the support frame, and the blank is positioned near the adhesive deposition area for applying adhesive to the blank.

2. The device according to claim 1, wherein the adhesive-directing surface extends along the Z axis in a non-parallel relationship and thereby diverges by at least 2 mm from the Z axis.

3. The device according to claim 1, wherein the adhesive-directing surface is non-parallel to the Z axis and has a tangent that is angled relative to the Z axis by at least 5 degrees.

4. The device according to claim 1, wherein the fixation wall further comprises a bonding zone adjacent the adhesive-directing surface.

5. The device according to claim 1, wherein the adhesive-directing surface provides at least a part of the through-hole that narrows from an exterior towards an interior of the through hole.

6. The device according to claim 1, wherein the adhesive-directing surface due to its shape is adapted to direct a flowable adhesive received on the adhesive-directing surface toward the bonding zone and thereby toward the blank.

7. The device according to claim 1, wherein the shape of the adhesive-directing surface comprises a beveled portion.

8. The device according to claim 1, having two opposing fixation walls each having an adhesive-directing surface and a bonding zone for affixation to two surfaces of the blank.

9. The device according to claim 8, wherein the blank is affixed at the bonding zones of the opposing fixation walls by an adhesive.

10. The device according to claim 8, wherein the adhesive is one of a chemically curing and thermosetting adhesive.

11. The device according to claim 1, wherein the through-hole has a cross-section of a generally rectangular shape.

12. The device according to claim 1, wherein a projection (P) of the blank in a direction of the Z axis onto a plane perpendicular to the Z axis is generally rectangular.

13. The device according to claim 12, having two opposing fixation walls each having an adhesive-directing surface and a bonding zone for affixation to two surfaces of the blank, wherein the projection (P) in at least one of its dimensions is smaller than the space between the bonding zones of the fixation walls.

14. The device according to claim 13, wherein the projection (P) is smaller by between 0.5 to 1.5 mm than the space between the bonding zones of the fixation walls.

15. The device according to claim 1, wherein the through-hole comprises an adhesive barrier to hinder adhesive that flows between the fixation wall and the blank in flowing past the adhesive barrier.

16. The device according to claim 1, wherein the blank is made of one of a pre-sintered ceramics and composite material.

17. The device according to claim 1, wherein the support frame has dimensionally stable guiding surfaces that allow it to be automatically handled in a machine for processing blanks.

18. The device according to claim 1, wherein the support frame is dimensioned so that the blank does not extend beyond the support frame in any direction.

19. The device according to claim 1, wherein the blank in a dimension parallel to the Z axis has a size that substantially corresponds to a distance between a top and a bottom of the support frame.

20. The device according to claim 1, wherein the support frame comprises a machine readable code.

21. The device according to claim 1, wherein the support frame has visible indicia.

22. The device according to claim 1, wherein the support frame is injection molded.

23. Method of affixing a blank within a support frame, comprising the steps of
    (i) positioning a blank within a through-hole of a support frame, the frame having a Z axis and comprising wall sections defining a through hole that extends along the Z axis through the frame, wherein at least one of the wall sections comprises an adhesive-directing surface having a generally convex cross-sectional shape, wherein the support frame has a T-shaped cross section supporting the convex surface near an adhesive deposition area, and at least one spacer is included on the wall sections, wherein the spacer does not extend across the entire through hole in any direction, wherein at least one of the wall sections forms a fixation wall for affixing the blank within the hole and positioned by the spacer, and wherein, when no adhesive is present, the blank can be accommodated in the hole in such a way that there is clearance between the blank and the fixation wall, wherein the width of the blank is smaller than the narrowest width of the through hole, wherein the blank has no direct contact with the support frame, and the blank is positioned near the adhesive deposition area for applying adhesive to the blank;
    (ii) dispensing adhesive on the adhesive-directing surface of the support frame and keeping the blank free of adhesive; and
    (iii) causing the adhesive to flow towards the blank and contact the blank.

24. Method of affixing a blank at a fixation wall of a support frame, comprising the steps of:
  (i) placing adhesive on an adhesive-directing surface of the support frame as a generally non-flowable deposit, the frame having a Z axis and comprising wall sections defining a through hole that extends along the Z axis through the frame, wherein at least one of the wall sections comprises an adhesive-directing surface having a generally convex cross-sectional shape, wherein the support frame has a T-shaped cross section supporting the convex surface near an adhesive deposition area, and at least one spacer is included on the wall sections, wherein the spacer does not extend across the entire through hole in any direction;
  (ii) positioning a blank within the through-hole of the support frame, wherein at least one of the wall sections forms a fixation wall for affixing the blank within the hole and positioned by the spacer, and wherein, when no adhesive is present, the blank can be accommodated in the hole in such a way that there is clearance between the blank and the fixation wall, wherein the width of the blank is smaller than the narrowest width of the through hole, wherein the blank has no direct contact with the support frame, and the blank is positioned near the adhesive deposition area for applying adhesive to the blank; and
  (iii) causing the adhesive to flow towards the blank and contact the blank.

* * * * *